United States Patent [19]
Freeman et al.

[11] Patent Number: 5,869,290
[45] Date of Patent: Feb. 9, 1999

[54] CAYAE1 POLYNUCLEOTIDES

[75] Inventors: Kathryn Belinda Freeman, King of Prussia; Richard Oakley Nicholas, Collegeville; George Pietro Livi, Havertown, all of Pa.

[73] Assignee: SmithKline Beecham Corporation, Philadelphia, Pa.

[21] Appl. No.: 752,132

[22] Filed: Nov. 21, 1996

[51] Int. Cl.$^6$ .............................. C12N 15/00; C07K 14/00
[52] U.S. Cl. ................ 435/69.1; 435/254.2; 435/254.11; 435/254.22; 435/257.3; 435/370.1; 536/23.1; 536/23.4; 536/23.5; 536/24.31; 530/350; 530/824; 424/274.1; 935/1; 935/19
[58] Field of Search .................................. 536/23.1, 23.4, 536/23.5, 24.31; 435/69.1, 320.1, 354.2, 254.11, 254.22, 252.3; 530/350, 824; 424/274.1; 935/1, 19

[56] References Cited

U.S. PATENT DOCUMENTS 4,879,213  11/1989  Fox et al. .
5,405,745  4/1995   Goman et al. .
5,529,916  6/1996   Cormack et al. .

OTHER PUBLICATIONS

*EMBO Journal*, 15:2031–2049, 1996.

scYAE1 homologue sequence fragment, *The homepage of the Candida albicans information pages on the Alces WWW server*, located at : http://alces.med.umn.edu/Candida.html available from the mapping project at the University of Minnesota.

Zha et al. Eur. J. Biochem. 1992, vol. 207, 305–313.

Lehniyan Biochemistry, new Ed. 1975, p. 63, Neonh Publishers, Inc., New York, N.Y.

Bringen et al. J. Cel Biol. 1990 vol. 111, 2129–2138.

Lazan et al. Mol. Cel. Biol. 1988, vol. 8 No. 3, 1247–1252.

*Primary Examiner*—Paula K. Hutzell
*Assistant Examiner*—Khalzd Masood
*Attorney, Agent, or Firm*—Edward R. Gimmi; William T. King

[57] ABSTRACT

The invention provides caYAE1 polypeptides and DNA (RNA) encoding such caYAE1 and a procedure for producing such polypeptides by recombinant techniques. Also provided are methods for utilizing such caYAE1 for the treatment of infection, particularly fungal infections. Antagonists against such caYAE1 and their use as a therapeutic to treat infections, particularly fungal infections are also provided. Further provided are diagnostic assays for detecting diseases related to the presence of caYAE1 nucleic acid sequences and the polypeptides in a host. Also provided are diagnostic assays for detecting polynucleotides encoding caYAE1 and for detecting the polypeptide in a host.

16 Claims, 4 Drawing Sheets

FIGURE 1. caYAE1 cloned DNA sequence [SEQ ID NO:1]

```
  1  GTGCACAAGT TATCAATTTG TTTATTATTA TAATTACACG GTAAAATCCC

51  AGTTTTCTTC TTAAACAATC TTCTTCTTCT TGTTCTTCTA ACATACAATT

101  TTATTTCAAT TCTACTTATA ACTTGACTCA TTTGATTCCA ATATTATACT

151  AATACAGTCT CTATACTTTC TTTTGCTTTT CTTTTTTTTT TTTTTTCATA

201  ATGACATGTC AAGAGGATTG TTCATGTAAG AATAATGAAG CCCCCACAAC

251  AAAGACAACT GCCACCACAA CTAATGTTGG TGATGGCCCT GGCCCTGGCC

301  CTATCCCTGG CAATAATGAT GATGTTGATG ATGACATTTG GTCAGATGAT

351  GATACGAAAC TAATACCTCA AAATGATATA ATACGATCAC ATTATAAAAA

401  AGGGTATGTT GATGGGATAA CTCAAGCTAA AGAATCTTCA TTACAACAAG

451  GATTTGATGA TGGATATCCT GAAGGTGCAA AATTAGGGAT TAAAGTTGGT

501  GAAATTTTAG CAAATTTAAT CAATCAATGT AAAGATAGAA ACAGACAAGG

551  AGATGATGAT GATGATGATG ATGAACAACT GGTAAGATTT AATGAAGCGA

601  AAAAGGAATT GAATATAGTT AATGTTTTAA AAAAATCTTA TTTTGATGAA

651  GATTTGAATT TGAAAAGAG TAATGGCAAT AAAGAAACTG ATGAATCATA

701  TCATGAATTA ATTAATAAAT GGGAGAATGA AATGAAATGA AATGACAGTA

751  AATTAAAATA GTATGTATAG ATATAGAAGT TGAAGGAATT ACTACTA
```

FIGURE 2. caYAE1 deduced amino acid sequence [SEQ ID NO:2]

```
  1  MTCQEDCSCK NNEAPTTKTT ATTTNVGDGP GPGPIPGNND DVDDDIWSDD

51  DTKLIPQNDI IRSHYKKGYV DGITQAKESS LQQGFDDGYP EGAKLGIKVG

101  EILANLINQC KDRNRQGDDD DDDDEQLVRF NEAKKELNIV NVLKKSYFDE

151  DLNLKKSNGN KETDESYHEL INKWENEMK
```

FIGURE 3 caYAE1 versus scYAE1 nucleotide sequence

```
300 CCTATCCCTGGCAATAATGATGATGTTGATGATGACATTTGGTCAGATGA 349
                ||||  |   || | ||      |            ||||
  1 ......ATGTCGAATACTTGGGACGATGTATGGGCATCAGACAGTGATGT  44

350 TGATACGAAACTAATACCTCAAAATGATATAATACGATCACATTAT...A 396
      || ||  ||| |   || |      |  |   || ||   || ||   |
 45 CGAAACTGAACGATCTCCAGATTTAGTGAAGTTAAGAGAGAATCATAGCA  94

397 AAAAAGGGTATGTTGATGGGATAACTCAAGCTAAAGAATCTTCATTACAA 446
     | |  |||||  | || || |||       ||||||||     |  |||
 95 AGAGGGGGTACTTGGACGGAATAGTGAGTTCTAAAGAAGAAAAGCTGCAA 144

447 CAAGGATTTGATGATGGATATCCTGAAGGTGCAAAATTAGGGATTAAAGT 496
     |  || ||  ||||||| |  ||    ||  || ||||||||||   ||||
145 GAGGGTTTCAATGATGGTTTCCCAACGGGCGCTAAATTAGGGAAACAAGT 194

497 TGGTGAAATTTTAGCAAATTTAATCAATCAATGTAAAGATAGAAACAGAC 546
    |||    ||||  | |  | ||| |                   |  ||
195 TGGCATAATTATGGGGATTTTACT.................TGGCCTAC  226

547 AAGGAGATGATGATGATGATGATGATGAACAACTGGTAAGATTTAATGAA 596
     |  |  |   || ||||||| ||||| || |            || ||  |||
227 GAACACGTTTTGGTGATGAAGATGAGGACCTCAGTAAGGCATATATTGAT 276

597 GCGAAAAAGGAATTGAATATAGTTAATGTTTTAAAAAAATCTTATTTTGA 646
    ||  ||||  |||||     ||   || ||  | |  || ||       |||||
277 GCTCAAAAGAATTACGCATTAACAAAGTACTTAGTAAGTCCATATTTGA  326

647 TGAAGATTTGAATTTGAAAAAGAGTAAT..GGCAATAAAGAAACTGATGA 694
     | | ||  |   ||| || | |   ||  |    |||| |||   ||
327 TCCAAACTTTGACTTGCAAGAAAAACATCCGCTCATAACAAAATGGACTG 376

695 ATCATATCATGAATTAATTAATAAATGGGAGAATGAAATGAAATGAAATG 744
    ||  | ||  |  ||  |||      |||         || ||  |   ||
377 ATATTGCCAATACCTATTGTGAAAAGTACCATGTGCCATCTATCCAAT.. 424
```

FIGURE 4   caYAE1 versus scYAE1 amino acid sequence

```
  1 MTCQEDCSCKNNEAPTTKTTATTTNVGDGPGPGPIPGNNDDVDDDIWSDD  50
                                  : . :.: :.:.||:.: :|.|
  1 ......................MSNTWDDVWASDSDVETE.RSPD  22

51 DTKLIPQNDIIRSHYKKGYVDGITQAKESSLQQGFDDGYPEGAKLGIKVG 100
    .|| ..        |  |:||:|||. .||..||:||:||:|.||||| .||
 23 LVKLREN......HSKRGYLDGIVSSKEEKLQEGFNDGFPTGAKLGKQVG  66

101 EILANLINQCKDRNRQGDDDDDDDEQLVRFNEAKKELNIVNVLKKSYFDE 150
    |:: |:.     |.| ||:|:|  ....:    :|.|||.| .||.||.||.
 67 IIMGILLGL...RTRFGDEDEDLSKAYI...DAQKELRINKVLSKSIFDP 110

151 DLNLKKSNGNKETDESYHELINKWENEMK............ 179
    :::|...         |.||.||.: .
111 NFDLQEK..........HPLITKWTDIANTYCEKYHVPSIQ 141
```

5,869,290

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 797 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

GTGCACAAGT TATCAATTTG TTTATTATTA TAATTACACG GTAAAATCCC AGTTTCTTC    60

| | | | | | |
|---|---|---|---|---|---|
| TTAAACAATC | TTCTTCTTCT | TGTTCTTCTA | ACATACAATT | TTATTTCAAT | TCTACTTATA | 120
| ACTTGACTCA | TTTGATTCCA | ATATTATACT | AATACAGTCT | CTATACTTTC | TTTTGCTTTT | 180
| CTTTTTTTTT | TTTTTCATA | ATGACATGTC | AAGAGGATTG | TTCATGTAAG | AATAATGAAG | 240
| CCCCCACAAC | AAAGACAACT | GCCACCACAA | CTAATGTTGG | TGATGGCCCT | GGCCCTGGCC | 300
| CTATCCCTGG | CAATAATGAT | GATGTTGATG | ATGACATTTG | GTCAGATGAT | GATACGAAAC | 360
| TAATACCTCA | AAATGATATA | ATACGATCAC | ATTATAAAAA | AGGGTATGTT | GATGGGATAA | 420
| CTCAAGCTAA | AGAATCTTCA | TTACAACAAG | GATTTGATGA | TGGATATCCT | GAAGGTGCAA | 480
| AATTAGGGAT | TAAAGTTGGT | GAAATTTTAG | CAAATTTAAT | CAATCAATGT | AAAGATAGAA | 540
| ACAGACAAGG | AGATGATGAT | GATGATGATG | ATGAACAACT | GGTAAGATTT | AATGAAGCGA | 600
| AAAAGGAATT | GAATATAGTT | AATGTTTTAA | AAAAATCTTA | TTTTGATGAA | GATTTGAATT | 660
| TGAAAAGAG | TAATGGCAAT | AAAGAAACTG | ATGAATCATA | TCATGAATTA | ATTAATAAAT | 720
| GGGAGAATGA | AATGAAATGA | AATGACAGTA | AATTAAAATA | GTATGTATAG | ATATAGAAGT | 780
| TGAAGGAATT | ACTACTA | | | | | 797

( 2 ) INFORMATION FOR SEQ ID NO:2:

( i ) SEQUENCE CHARACTERISTICS:
        ( A ) LENGTH: 179 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Met  Thr  Cys  Gln  Glu  Asp  Cys  Ser  Cys  Lys  Asn  Asn  Glu  Ala  Pro  Thr
 1              5                        10                       15

Thr  Lys  Thr  Thr  Ala  Thr  Thr  Thr  Asn  Val  Gly  Asp  Gly  Pro  Gly  Pro
             20                        25                       30

Gly  Pro  Ile  Pro  Gly  Asn  Asn  Asp  Asp  Val  Asp  Asp  Asp  Ile  Trp  Ser
             35                        40                       45

Asp  Asp  Asp  Thr  Lys  Leu  Ile  Pro  Gln  Asn  Asp  Ile  Ile  Arg  Ser  His
        50                        55                       60

Tyr  Lys  Lys  Gly  Tyr  Val  Asp  Gly  Ile  Thr  Gln  Ala  Lys  Glu  Ser  Ser
 65                       70                       75                      80

Leu  Gln  Gln  Gly  Phe  Asp  Asp  Gly  Tyr  Pro  Glu  Gly  Ala  Lys  Leu  Gly
                      85                       90                       95

Ile  Lys  Val  Gly  Glu  Ile  Leu  Ala  Asn  Leu  Ile  Asn  Gln  Cys  Lys  Asp
                     100                      105                      110

Arg  Asn  Arg  Gln  Gly  Asp  Asp  Asp  Asp  Asp  Asp  Glu  Gln  Leu  Val
             115                      120                      125

Arg  Phe  Asn  Glu  Ala  Lys  Lys  Glu  Leu  Asn  Ile  Val  Asn  Val  Leu  Lys
             130                      135                      140

Lys  Ser  Tyr  Phe  Asp  Glu  Asp  Leu  Asn  Leu  Lys  Lys  Ser  Asn  Gly  Asn
145                      150                      155                     160

Lys  Glu  Thr  Asp  Glu  Ser  Tyr  His  Glu  Leu  Ile  Asn  Lys  Trp  Glu  Asn
                     165                      170                      175
```

Glu Met Lys ( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

GGATTTGATG ATGGATATCC    20

( 2 ) INFORMATION FOR SEQ ID NO:4:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

AATTCCTTTT TCGCTTCATT AAAT    24

CAYAE1 POLYNUCLEOTIDES

This invention relates, in part, to newly identified polynucleotides and polypeptides; variants and derivatives of these polynucleotides and polypeptides; processes for making these polynucleotides and these polypeptides, and their variants and derivatives; agonists and antagonists of the polypeptides; and uses of these polynucleotides, polypeptides, variants, derivatives, agonists and antagonists. In particular, in these and in other regards, the invention relates to polynucleotides and polypeptides derived from a *Candida albicans* gene, hereinafter all such polynucleotides and polypeptides are referred to as "caYAE1".

BACKGROUND OF THE INVENTION

The *Saccharomyces cerevisiae* genome project has identified many unknown, hypothetical proteins (EMBO Journal 15, 2031–2049, 1996). These sequences may be a useful starting point for the discovery of biologically important sequences. Using these sequences as research tools to discover essential genes is one of their uses. Discovering and understanding essential genes in pathogenic organisms provides reagents to screen for antipathogen compounds.

Many techniques are available to identify genes which are essential to survival per se, or essential to the establishment/maintenance of an infection. These techniques include, for example, differential display (Chuang et al., *J. Bacteriol.* 175:2026–2036 (1993)), generation of conditional lethal mutants by transposon mutagenesis (de Lorenzo, V. et al., *Gene* 123:17–24 (1993); Neuwald, A. F. et al., *Gene* 125: 69–73(1993); and Takiff, H. E. et al., *J. Bacteriol.* 174:1544–1553(1992)), and generation of conditional lethal mutants by chemical mutagenesis (Beckwith, J., *Methods in Enzymology* 204: 3–18(1991)). Certain of these techniques were applied to discover the genetic sequences of the present invention, caYAE1. Clearly, there is a need for factors, such as essential polynucleotide and polypeptides from fungal pathogens, since they may be used to screen compounds for antifungal activity and which may also be used to determine their roles in pathogenesis of infection, dysfunction and disease. There is a need, therefore, for identification and characterization of such factors which can play a role in preventing, ameliorating or correcting infections, dysfunctions or diseases.

The polypeptide of the present invention has amino acid sequence homology to known essential protein YAE1 of *Saccharomyces cerevisiae* hereinafter referred to as "scYAE1."

SUMMARY OF THE INVENTION

Toward these ends, and others, it is an object of the present invention to provide polypeptides, inter alia, that have been identified as novel caYAE1 peptides by homology between the amino acid sequence set out in FIG. 2 and known amino acid sequences of other proteins such as scYAE1 protein.

It is a further object of the invention, moreover, to provide polynucleotides that encode caYAE1 polypeptides, particularly polynucleotides that encode the polypeptide herein designated caYAE1.

In a particularly preferred embodiment of this aspect of the invention the polynucleotide comprises the region encoding caYAE1 polypeptides in the sequence set out in FIG. 1 [SEQ ID NO:1], or a fragment, analogue or derivative thereof.

In another particularly preferred embodiment of the present invention there is a novel protein from *Candida albicans* comprising the amino acid sequence of FIG. 2 [SEQ ID NO:2], or a fragment, analogue or derivative thereof.

In accordance with this aspect of the invention there are provided isolated nucleic acid molecules encoding *Candida albicans* YAE1, including mRNAs, cDNAs, genomic DNAs and, in further embodiments of this aspect of the invention include biologically, diagnostically, prophylactically, clinically or therapeutically useful variants, analogs or derivatives thereof, or fragments thereof, including fragments of the variants, analogs and derivatives, and compositions comprising same.

In accordance with another aspect of the present invention, there is provided the use of a polynucleotide of the invention for therapeutic or prophylactic purposes, in particular genetic immunization.

Among the particularly preferred embodiments of this aspect of the invention are naturally occurring allelic variants of caYAE1 and polypeptides encoded thereby.

In accordance with this aspect of the invention there are provided novel polypeptides of Candida referred to herein as caYAE1 as well as biologically, diagnostically, prophylactically, clinically or therapeutically useful fragments, variants and derivatives thereof, variants and derivatives of the fragments, and analogs of the foregoing, and compositions comprising same.

Among the particularly preferred embodiments of this aspect of the invention are variants of caYAE1 polypeptide encoded by naturally occurring alleles of the caYAE1 gene.

In a preferred embodiment of this aspect of the invention there are provided methods for producing the aforementioned caYAE1 polypeptides.

In accordance with yet another aspect of the present invention, there are provided inhibitors to such polypeptides, useful as antifungal agents, including, for example, antibodies.

In accordance with certain preferred embodiments of this aspect of the invention, there are provided products, compositions and methods, inter alia: assessing caYAE1 expression; to treat, for example, candidosis (candidiasis), for example, superficial candidosis; candidosis of the oropharynx, such as, oral thrush (acute pseudomembraneous candodisis), denture stomatitis, angular choilitis (perlèche), Candida leukoplakia (chronic hyperplastic candidosis), midline glossitis (median rbomboid glossitis, glossal central papillary atrophy, "antibiotic sore tongue", acute atrophic candidosis), and miscellaneous forms of oral candidosis; candidosis of the genitalia, such as, vulvovaginal candidosis (vaginal thrush, Candida colpitis), and candidosis of the penis (Candida balanitis, balanoposthitis and urethritis); candidosis of the skin, nails and other external sites, such as, Candida intertrigo, napkin (diaper) dermatitis, Candida onychia and paronychia, candidosis of the external ear, and miscellaneous cutaneous forms of candidosis; chronic mucocutaneous candidosis; systemic candidosis; candidosis of the gastrointestinal tract, such as, esophageal candidosis, gastric candidosis, candidosis of the intestine, Candida cholecystitis, and the "autobrewery syndrome" ("meiteisho"); candidosis of the Urinary Tract, such as, renal candidosis (Candida pyelonephritis), candidosis of the urinary bladder (Candida cystitis), Candida urethritis and prostatitis; cardiovascular Candida infections, such as, candida endocarditis, and myocarditis; Candida endocariditis, Candida myocarditis and pericarditis, Candida phlebitis and thrombophlebitis; Candida infections of the eye, such as, Candida endophthalmitis, Candida infections of the cornea and conjuctiva, and candidosis of the lacrimal sacs (dacryocystitis); candidosis of the central nervous system; Candida meningitis, cerebral candidosis, and candidosis of the inner ear; Candida infections of bones and joints; Candida peritonitis, hepatitis and miscellaneous other forms of systemic candidosis, such as, Candida peritonitis, Candida hepatitis and splenitis, Candida pancreatitis, Congenital and intrauterine candidosis (Candida chorioamnionitis and funisitis); disseminated candidosis, such as, in neonates, young infants, and heroin addicts; Candida allergy, such as, cutaneous Candida allergy and "candidids", Respiratory tract allergy to "Candida", Candida allergy in other bodily sites, "chronic candidosis" and "the yeast connection"; and also for assaying genetic variation; and for administering a caYAE1 polypeptide or polynucleotide to an organism to raise an immunological response against a fungi, for example, opportunistic fungi, especially a Candida or Aspergillus.

In accordance with certain preferred embodiments of this and other aspects of the invention there are provided polynucleotides that hybridize to caYAE1 polynucleotide sequences.

In certain additional preferred embodiments of this aspect of the invention there are provided antibodies against caYAE1 polypeptides.

In accordance with another aspect of the present invention, there are provided caYAE1 agonists which are also preferably bacteriostatic or bacteriocidal.

In accordance with yet another aspect of the present invention, there are provided caYAE1 antagonists which are also preferably bacteriostatic or bacteriocidal.

In a further aspect of the invention there are provided compositions comprising a caYAE1 polynucleotide or a caYAE1 polypeptide for administration to a cell or to a multicellular organism.

Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the polynucleotide sequence of *Candida albicans* YAE1, caYAE1 [SEQ ID NO:1]. The open reading frame of caYAE1 is from nucleotide 201 to 737.

FIG. 2 shows the amino acid sequence of *Candida albicans* YAE1, caYAE1 [SEQ ID NO:2] deduced from the polynucleotide sequence of FIG. 1.

FIG. 3 shows the nucleotide sequence of the *S. cerevisiae* and *C. albicans* YAE1 genes which are 50% identical FIG. 4 shows the amino acid sequence of the *S. cerevisiae* and *C. albicans* YAE1 proteins. The deduced protein sequence is shown in this Figure. The caYae1p (from *C. albicans*) is 179 amino acids in length and 42% identical, 60% similar to scYae1p (from *S. ceriviseae*) which is 121 amino acids in length.

GLOSSARY

The following illustrative explanations are provided to facilitate understanding of certain terms used frequently herein, particularly in the Examples. The explanations are provided as a convenience and are not limitative of the invention. caYAE1-BINDING MOLECULE, as used herein, refers to molecules or ions which bind or interact specifically with caYAE1 polypeptides or polynucleotides of the present invention, including, for example enzyme substrates, cell membrane components and classical receptors. Binding between polypeptides of the invention and such molecules, including binding or binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL is a cell which has been transformed or transfected, or is capable of transformation or transfection by an exogenous polynucleotide sequence.

IDENTITY or SIMILARITY, as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two polynucleotide or two polypeptide sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM J. *Applied Math.*, 48: 1073 (1988). Methods commonly employed to determine identity or similarity between sequences include, but are not limited to those disclosed in Carillo, H., and Lipman, D., SIAM J. *Applied Math.*, 48:1073 (1988). Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403 (1990)).

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS—STRUCTURE AND MOLECULAR PROPERTIES*, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modifications and Aging*, Ann. N. Y. Acad. Sci. 663: 48–62 (1992). It will be appreciated, as is well known and as noted above, that polypeptides are not always entirely linear. For instance, polypeptides may be generally as a result of posttranslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in fungal hosts such as, for example, S. ceriviseae. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination.

DETAILED DESCRIPTION OF THE INVENTION

The present invention relates to novel caYAE1 polypeptides and polynucleotides, among other things, as described in greater detail below. In particular, the invention relates to polypeptides and polynucleotides of a novel caYAE1 gene of Candida albicans, which is related by amino acid sequence homology to the YAE1 polypeptide of Saccharomyces cerevisiae. The invention relates especially to caYAE1 having the nucleotide and amino acid sequences set out in FIG. 1 and FIG. 2 respectively. The nucleotide and amino acid sequences set out in FIGS. 1 [SEQ ID NO:1] and 2 [SEQ ID NO:2] were obtained by sequencing the C. albicans DNA.

Techniques are available to evaluate temporal gene expression in fungi, particularly as it applies to viability under laboratory and host infection conditions. A number of methods can be used to identify genes which are essential to survival per se, or essential to the establishment/maintenance of an infection. Identification of expression of a sequence by one of these methods yields additional information about its function and permits the selection of such sequence for further development as a screening target. Briefly, these approaches include:

1) Differential display

This technique is described by Chuang et al., J. Bacteriol. 175:2026–2036(1993), the contents of which is incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to library sequences.

2) Generation of conditional lethal mutants by transposon mutagenesis.

This technique, described by de Lorenzo, V. et al., Gene 123:17–24 (1993); Neuwald, A. F. et al., Gene 125: 69–73 (1993); and Takiff, H. E. et al., J. Bacteriol. 174:1544–1553 (1992), the contents of which is incorporated by reference for background purposes, identifies genes whose expression are essential for cell viability.

In this technique transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, peptidoglycan, monitoring reporter enzyme gene fusions which respond to known cellular stresses.

3) Generation of conditional lethal mutants by chemical mutagenesis.

This technique is described by Beckwith, J., Methods in Enzymology 204: 3–18(1991), the contents of which are incorporated herein by reference for background purposes. In this technique random chemical mutagenesis of target organism, growth at temperature other than physiological temperature (permissive temperature) and subsequent replica plating and growth at different temperature (e.g., 42° C. to identify ts, 25° C. to identify cs) are used to identify those isolates which now fail to grow (conditional mutants). As above close monitoring of the changes upon growth at the non-permissive temperature yields information on the function of the mutated gene. Complementation of conditional lethal mutation by library from target organism and sequencing of complementing gene allows matching with library sequences.

4) RT-PCR

Fungal messenger RNA, preferably that of *Candida albicans*, is isolated from fungal infected tissue e.g. 48 hour murine lung infections, and the amount of each MRNA species assessed by reverse transcription of the RNA sample primed with random hexanucleotides followed by PCR with gene specific primer pairs. The determination of the presence and amount of a particular mRNA species by quantification of the resultant PCR product provides information on the fungal genes which are transcribed in the infected tissue. Analysis of gene transcription can be carried out at different times of infection to gain a detailed knowledge of gene regulation in fungal pathogenesis allowing for a clearer understanding of which gene products represent targets for screens for novel antifungals. Because of the gene specific nature of the PCR primers employed it should be understood that the fungal mRNA preparation need not be free of mammalian RNA. This allows the investigator to carry out a simple and quick RNA preparation from infected tissue to obtain fungal mRNA species which are very short lived in the bacterium (in the order of 2 minute halflives). Optimally the fungal MRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimized by finding those conditions which give a maximum amount of fungal 16S ribosomal RNA, preferably that of *Candida albicans*, as detected by probing Northerns with a suitably labeled sequence specific oligonucleotide probe. Typically a 5' dye labelled primer is used in each PCR primer pair in a PCR reaction which is terminated optimally between 8 and 25 cycles. The PCR products are separated on 6% polyacrylamide gels with detection and quantification using GeneScanner (manufactured by ABI).

5) Targeted gene disruption

This technique is described by Fonzi, W. A. and Irwin, M. Y. *Genetics* 134: 717–728 (1993), the contents of which are incorporated herein by reference for background purposes. In this technique a selectable marker flanked by direct repeats is inserted into the gene of interest. This construct is then integrated into the genome by homologous recombination, selecting for the expression of the marker and thereby disrupting the targeted gene. The marker gene can be removed by homologous recombination of the flanking sequences leaving behind a single copy of the direct repeat sequence which disrupts the targeted gene. Integration of the disruption cassette can then be repeated allowing for disruption of multiple alleles of the targeted gene. As above close monitoring of the changes upon growth after gene disruption yields information on the function of the mutated gene.

Each of these techniques may have advantages or disadvantage depending on the particular application. The skilled artisan would choose the approach that is the most relevant with the particular end use in mind. For example, some genes might be recognised as essential for infection but in reality are only necessary for the initiation of infection and so their products would represent relatively unattractive targets for antifungals developed to cure established and chronic infections.

Use of the of these technologies when applied to the sequences of the present invention enables identification of fungal proteins expressed during infection, inhibitors of which would have utility in anti-fungal therapy.

Polynucleotides

In accordance with one aspect of the present invention, there are provided isolated polynucleotides which encode the caYAE1 polypeptide having the deduced amino acid sequence of FIG. 2 [SEQ ID NO:2].

This invention provides, among other things, that one of the hypothetical *S. ceriviseae* proteins disclosed in EMBO Journal 15, 2031–2049, 1996, encoded by the ORF YJR067c, is essential for the growth of wild-type yeast. In view of this, strains were isolated which have a null chromosomal mutation in YJR067c, with viability being dependent upon the presence of a plasmid carrying a wild-type copy of YJR067c. This indicated that loss of the chromosomal YJR067c protein is lethal. This was confirmed by direct construction of a YJR067c deletion/insertion mutation in a diploid strain, followed by sporulation and tetrad dissection; haploid YJR067c-deleted segregants were never recovered, indicating that YJR067c is an essential gene. The protein was tagged with a T7 epitope and a polypeptide of the expected size was observed by western analysis (YJR067c encodes a 141-amino acid protein). Reverse transcription PCR assays also confirmed that YJR067c is an expressed gene (herein "scYAE1").

The scYAE1 coding region was found among a collection of randomly cloned and sequenced *S. ceriviseae* clones. Cross-species Southern blots ("zoo blots") did not identify any potential mammalian homologues. A *Candida albicans* clone was, however, identified from a database of sequence fragments, which is a scYAE1 homologue sequence fragment (the homepage of the *Candida albicans* information pages on the Alces WWW server is located at: http://alces.med.umn.edu/Candida.html available from the mapping project at the University of Minnesota). The *C. albicans* clone (clone 2115) is 49% identical at the nucleotide level to scYAE1. Oligonucleotide probes were designed from the *C. albicans* sequence and used to isolate a full-length YAE1 homologue from a *C. albicans* genomic library carried in the plasmid YEp13 (Mol. Gen. Genet. 200. 500–502, 1985). Seven isolates representing 2 individual, overlapping clones were isolated. Subdlones of these two clones were sequenced and shown to contain an ORF encoding a 179 amino acid protein caYAE1 which is 42% identical, 60% similar to *S. cerevisiae* scYAE1 protein. The sequence of the *C. albicans* caYAE1 gene is shown in the attachment. The *C. albicans* clone is unable to complement the lethal phenotype of a scYAE1-deletion in *S. cerevisiae*, but this may be due to the inability of *S. cerevisiae* to utilize the Candida promoter. Interestingly, complementation can be achieved using a plasmid carrying the *S. cerevisiae* scYAE1 coding region under control of the galactose-inducible GAL1 promoter even in the presence of glucose, suggesting that very little scYAE1 is required to support viability.

Using the information provided herein, such as the polynucleotide sequence set out in FIG. 1 [SEQ ID NO:1], a polynucleotide of the present invention encoding caYAE1 polypeptide may be obtained using standard cloning and screening procedures, such as those for cloning and sequencing chromosomal DNA fragments from *Candida albicans* B792 cells as starting material, followed by obtaining a full length clone. For example, to obtain a polynucleotide of the invention sequence, such as that sequence given in FIG. 1 [SEQ ID NO: 1] typically a library of clones of chromosomal DNA of *Candida albicans* B792 in *S. ceriviseae*, Aspergillus, *E. coli* or some other suitable host is probed with a radiolabeled oligonucleotide, preferably a 17-mer or longer, derived from a partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70). Illustrative of the invention, the polynucleotide set out in FIG. 1 [SEQ ID NO:1] was discovered in a DNA library derived from *Candida albicans* B792.

caYAE1 of the invention is structurally related to other proteins of the YAE1 family, as shown by the results of sequencing the DNA encoding caYAE1. The DNA sequence thus obtained is set out in FIG. 1 [SEQ ID NO:1]. It contains an open reading frame encoding a protein of having about the number of amino acid residues set forth in FIG. 2 [SEQ ID NO:2] with a deduced molecular weight that can be calculated using amino acid residue molecular weight values well known in the art. FIG. 3 shows a sequence alignment. The nucleotide sequence of the ORFs of the *S. cerevisiae* and *C. albicans* caYAE1 genes are 50% identical. The portion of the caYAE1 sequence which was identified from a set of randomly sequenced *Candida albicans* clones (designated clone 2115) spans from nucleotide 285 to 797. The original clone identified, 2115, lacked a portion of the 5' end of the open reading frame and had some gaps in the sequence.

The protein exhibits greatest homology to *Saccharomyces cerevisiae* YAE1 protein among known proteins. caYAE1 of FIG. 2 [SEQ ID NO:2] has about 42% identity over its entire length and about 60% similarity over its entire length with the amino acid sequence of scYAE1 polypeptide. FIG. 4 shows an alignment of the caYAE1 and scYAE1 amino acid sequences.

Polynucleotides of the present invention may be in the form of RNA, such as MRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1 [SEQ ID NO:1]. It also may be a polynucleotide with a different sequence, which, as a result of the redundancy (degeneracy) of the genetic code, encodes the polypeptide of FIG. 2 [SEQ ID NO:2].

Polynucleotides of the present invention which encode the polypeptide of FIG. 2 [SEQ ID NO:2] may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. Thus, for instance, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci., USA* 86: 821–824 (1989), for instance, hexa-histidine provides for convenient purification of the fusion protein. The HA tag may also be used to create fusion proteins and corresponds to an epitope derived of influenza hemagglutinin protein, which has been described by Wilson et al., *Cell* 37: 767 (1984), for instance. Polynucleotides of the invention also include, but are not limited to, polynucleotides comprising a structural gene and its naturally associated genetic elements.

In accordance with the foregoing, the term "polynucleotide encoding a polypeptide" as used herein encompasses polynucleotides which include a sequence encoding a polypeptide of the present invention, particularly fungal, and more particularly the *Candida albicans* YAE1 having the amino acid sequence set out in FIG. 2 [SEQ ID NO:2]. The term encompasses polynucleotides that include a single continuous region or discontinuous regions encoding the polypeptide (for example, interrupted by insertion sequence, introns or editing) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 2 [SEQ ID NO:2]. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of caYAE1 set out in FIG. 2 [SEQ ID NO:2]; variants, analogs, derivatives and fragments thereof, and fragments of the variants, analogs and derivatives.

Further particularly preferred in this regard are polynucleotides encoding caYAE1 variants, analogs, derivatives and fragments, and variants, analogs and derivatives of the fragments, which have the amino acid sequence of caYAE1 polypeptide of FIG. 2 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of caYAE1. Also especially preferred in this regard are conservative substitutions. Most highly preferred are polynucleotides encoding polypeptides having the amino acid sequence of FIG. 2 [SEQ ID NO:2], without substitutions.

Further preferred embodiments of the invention are polynucleotides that are at least 70% identical over their entire length to a polynucleotide encoding caYAE1 polypeptide having the amino acid sequence set out in FIG. 2 [SEQ ID NO:2], and polynucleotides which are complementary to such polynucleotides. Alternatively, most highly preferred are polynucleotides that comprise a region that is at least 80% identical over their entire length to a polynucleotide encoding caYAE1 polypeptide of the *Candida albicans* DNA and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments in this respect, moreover, are polynucleotides which encode polypeptides which retain substantially the same biological function or activity as the mature polypeptide encoded by the DNA of FIG. 1 [SEQ ID NO:1].

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding caYAE1 and to isolate cDNA and genomic clones of other genes that have a high sequence similarity to the caYAE1 gene. Such probes generally will comprise at least 15 bases. Preferably, such probes will have at least 30 bases and may have at least 50 bases. Particularly preferred probes will have at least 30 bases and will have 50 bases or less. An example of a probe useful to detect the polynucleotide of the invention is 5'-ggatttgatgatggatatcc-3' [SEQ ID NO:3].

For example, the coding region of the caYAE1 gene may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine which members of the library the probe hybridizes to.

The polynucleotides and polypeptides of the present invention may be employed as research reagents and materials for discovery of treatments of and diagnostics for disease, particularly human disease, as further discussed herein relating to polynucleotide assays, inter alia.

The polynucleotides of the invention that are oligonucleotides, including SEQ ID NOS:3 and 4, derived from the sequences of SEQ ID NO:1 may be used in the processes herein as described, but preferably for PCR, to determine whether or not the Candida albicans genes identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to a caYAE1 polypeptide which has a deduced amino acid sequence of 179 amino acids in length, as set forth in FIG. 2 [SEQ ID NO:2].

The invention also relates to fragments, analogs and derivatives of these polypeptides. The terms "fragment," "derivative" and "analog" when referring to the polypeptide of FIG. 2 [SEQ ID NO:2], means a polypeptide which retains essentially the same biological function or activity as such polypeptide. Thus, an analog includes a proprotein which can be activated by cleavage of the proprotein portion to produce an active mature polypeptide.

The fragment, derivative or analog of the polypeptide of FIG. 2 [SEQ ID NO:2] may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of caYAE1 set out in FIG. 2 [SEQ ID NO:2], variants, analogs, derivatives and fragments thereof, and variants, analogs and derivatives of the fragments.

Alternatively, particularly preferred embodiments of the invention in this regard are polypeptides having the amino acid sequence of the caYAE1, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the caYAE1 polypeptide of FIG. 2 [SEQ ID NO:2], in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the caYAE1. Also especially preferred in this regard are conservative substitutions. Most highly preferred are polypeptides having the amino acid sequence of FIG. 2 [SEQ ID NO:2] without substitutions.

The polypeptides and polynucleotides of the present invention are preferably provided in an isolated form, and preferably are purified to homogeneity.

The polypeptides of the present invention include the polypeptide of FIG. 2 [SEQ ID NO:2] (in particular the mature polypeptide) as well as polypeptides which have at least 70% identity to the polypeptide of FIG. 2 [SEQ ID NO:2], preferably at least 80% identity to the polypeptide of FIG. 2 [SEQ ID NO:2], and more preferably at least 90% similarity (more preferably at least 90% identity) to the polypeptide of FIG. 2 [SEQ ID NO:2] and still more preferably at least 95% similarity (still more preferably at least 95% identity) to the polypeptide of FIG. 2 [SEQ ID NO:2] and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of caYAE1, most particularly fragments of caYAE1 having the amino acid set out in FIG. 2 [SEQ ID NO:2], and fragments of variants and derivatives of the caYAE1 of FIG. 2 [SEQ ID NO:2].

In this regard a fragment is a polypeptide having an amino acid sequence that entirely is the same as part but not all of the amino acid sequence of the aforementioned caYAE1 polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a caYAE1 polypeptide of the present comprised within a precursor polypeptide designed for expression in a host and having heterologous pre and pro-polypeptide regions fused to the amino terminus of the caYAE1 fragment and an additional region fused to the carboxyl terminus of the fragment. Therefore, fragments in one aspect of the meaning intended herein, refers to the portion or portions of a fusion polypeptide or fusion protein derived from caYAE1.

Representative examples of polypeptide fragments of the invention, include, for example, fragments from amino acid number 1–20, 21–40, 41–60, 61–80, 81–100, and 101–120, 121–140, 141–160, 161–179, and any combination of these amino acid fragments.

In this context "about" herein includes the particularly recited ranges larger or smaller by several, a few, 5, 4, 3, 2 or 1 amino acid at either extreme or at both extremes.

Preferred fragments of the invention include, for example, truncation polypeptides of caYAE1. Truncation polypeptides include caYAE1 polypeptides having the amino acid sequence of FIG. 2, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally. Degradation forms of the polypeptides of the invention in a host cell, particularly a Candida, are also preferred.

Also preferred in this aspect of the invention are fragments characterized by structural or functional attributes of caYAE1. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions of caYAE1, and combinations of such fragments.

Preferred regions are those that mediate activities of caYAE1. Most highly preferred in this regard are fragments that have a chemical, biological or other activity of caYAE1, including those with a similar activity or an improved activity, or with a decreased undesirable activity. Further preferred polypeptide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, host cells, expression

The present invention also relates to vectors which comprise a polynucleotide or polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989).

Polynucelotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from fungal plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct mRNA transcription. Representatives of such promoters include, but are not limited to, the phage lambda PL promoter, the E. coli lac, trp and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating codon, for example, AUG, at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers and amplification regions, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

Representative examples of appropriate hosts include bacterial cells, such as streptococci, staphylococci, E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the E. coli lacd and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and met allothionein promoters, such as the mouse met allothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the codon that initiates translation of the polypeptide to be expressed, for example AUG or GUG. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar are familiar and routine techniques in the art. A preferred fusion protein comprises a heterologous region from immunolglobulin that is useful to solubilize or purify polypeptides. For example, EP-A-O 464 533 (Canadian counterpart 2045869) discloses fusion proteins comprising various portions of constant region of immunoglobin molecules together with another protein or part thereof. In drug discovery, for example, proteins have been fused with antibody Fc portions for the purpose of high-throughput screening assays to identify antagonists. See, D. Bennett et al., *Journal of Molecular Recognition, Vol.* 8 52–58 (1995) and K. Johanson et al., The *Journal of Biological Chemistry, Vol.* 270, No. 16, pp 9459–9471 (1995).

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Mammalian expression vectors may comprise an origin of replication, a suitable promoter and enhancer, and also any necessary ribosome binding sites, polyadenylation regions, splice donor and acceptor sites, transcriptional termination sequences, and 5' flanking non-transcribed sequences that are necessary for expression. caYAE1 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Polynucleotide assays

This invention is also related to the use of the caYAE1 polynucleotides to detect complementary polynucleotides such as, for example, as a diagnostic reagent. Detection of caYAE1 in a eukaryote, particularly a mammal, and especially a human, will provide a diagnostic method for diagnosis of a disease. Eukaryotes (herein also "individual(s)"), particularly mammals, and especially humans, infected with an organism comprising the caYAE1 gene may be detected at the DNA level by a variety of techniques. Nucleic acids for diagnosis may be obtained from an infected individual's cells and tissues, such as bone, blood, muscle, cartilage, and skin. Genomic DNA may be used directly for detection or may be amplified enzymatically by using PCR (Saiki et al., *Nature,* 324: 163–166 (1986) prior to analysis. RNA or cDNA may also be used in the same ways. As an example, PCR primers complementary to the nucleic acid encoding caYAE1 can be used to identify and analyze caYAE1 presence and/or expression. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled caYAE1 RNA or alternatively, radiolabeled caYAE1 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic characterization based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230: 1242 (1985)).

Sequence changes at specific locations also may be revealed by nuclease protection assays, such as RNase and S1 protection or the chemical cleavage method (e.g., Cotton et al., *Proc. Natl. Acad. Sci., USA*, 85: 4397–4401 (1985)).

Thus, the detection of a specific DNA sequence may be achieved by methods such as hybridization, RNase protection, chemical cleavage, direct DNA sequencing or the use of restriction enzymes, e.g., restriction fragment length polymorphisms (RFLP) and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for serotyping, for example. For example, RT-PCR can be used to detect mutations. It is particularly preferred o used RT-PCR in conjunction with automated detection systems, such as, for example, GeneScan. RNA or cDNA may also be used for the same purpose, PCR or RT-PCR. As an example, PCR primers complementary to the nucleic acid encoding caYAE1 can be used to identify and analyze mutations. Examples of representative primers are shown below in Table 1.

TABLE 1

Primers used for amplification of caYAE1 polynucleotides

| SEQ ID NO | PRIMER SEQUENCE |
|---|---|
| 3 | 5'-ggatttgatgatggatatcc-3' |
| 4 | 5'-aattccttttttcgcttcattaaat-3' |

These primers may be used for amplifying caYAE1 DNA isolated from a sample derived from an individual. The invention also provides the primers of Table 1 with 1, 2, 3 or 4 nucleotides removed from the 5' and/or the 3' end. The primers may be used to amplify the gene isolated from the individual such that the gene may then be subject to various techniques for elucidation of the DNA sequence. In this way, mutations in the DNA sequence may be diagnosed.

The invention provides a process for diagnosing, disease, preferably fungal infections, more preferably *Candida albicans* infections, and most preferably candidosis (candidiasis), for example, superficial candidosis; candidosis of the oropharynx, such as, oral thrush (acute pseudomembraneous candodisis), denture stomatitis, angular choilitis (perleche), Candida leukoplakia (chronic hyperplastic candidosis), midline glossitis (median rbomboid glossitis, glossal central papillary atrophy, "antibiotic sore tongue", acute atrophic candidosis), and miscellaneous forms of oral candidosis; candidosis of the genitalia, such as, vulvovaginal candidosis (vaginal thrush, Candida colpitis), and candidosis of the penis (Candida balanitis, balanoposthitis and urethritis); candidosis of the skin, nails and other external sites, such as, Candida intertrigo, napkin (diaper) dermatitis, Candida onychia and paronychia, candidosis of the external ear, and miscellaneous cutaneous forms of candidosis; chronic mucocutaneous candidosis; systemic candidosis; candidosis of the gastrointestinal tract, such as, esophageal candidosis, gastric candidosis, candidosis of the intestine, Candida cholecystitis, and the "autobrewery syndrome" ("meitei-sho"); candidosis of the Urinary Tract, such as, renal candidosis (Candida pyelonephritis), candidosis of the urinary bladder (Candida cystitis), Candida urethritis and prostatitis; cardiovascular Candida infections, such as, candida endocarditis, and myocarditis; Candida endocariditis, Candida myocarditis and pericarditis, Candida phlebitis and thrombophlebitis; Candida infections of the eye, such as, Candida endophthalmitis, Candida infections of the cornea and conjuctiva, and candidosis of the lacrimal sacs (dacryocystitis); candidosis of the central nervous system; Candida meningitis, cerebral candidosis, and candidosis of the inner ear; Candida infections of bones and joints; Candida peritonitis, hepatitis and miscellaneous other forms of systemic candidosis, such as, Candida peritonitis, Candida hepatitis and splenitis, Candida pancreatitis, Congenital and intrauterine candidosis (Candida chorioamnionitis and funisitis); disseminated candidosis, such as, in neonates, young infants, and heroin addicts; Candida allergy, such as, cutaneous Candida allergy and "candidids", Respiratory tract allergy to "Candida", Candida allergy in other bodily sites, "chronic candidosis" and "the yeast connection," comprising determining from a sample derived from an individual an increased level of expression of polynucleotide having the sequence of FIG. 1 [SEQ ID NO: 1]. Increased expression of caYAE1 polynucleotide can be measured using any one of the methods well known in the art for the quantitation of polynucleotides, such as, for example, PCR, RT-PCR, RNase protection, Northern blotting and other hybridization methods.

Polypeptide assays

The present invention also relates to a diagnostic assays such as quantitative and diagnostic assays for detecting levels of caYAE1 protein in cells and tissues, including determination of normal and abnormal levels. Thus, for instance, a diagnostic assay in accordance with the invention for detecting over-expression of caYAE1 protein compared to normal control tissue samples may be used to detect the presence of an infection, for example. Assay techniques that can be used to determine levels of a caYAE1 protein, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to caYAE1, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

Antibodies

The polypeptides, their fragments or other derivatives, or analogs thereof, or cells expressing them can be used as an immunogen to produce antibodies thereto. The present invention includes, for examples monoclonal and polyclonal antibodies, chimeric, single chain, and humanized antibodies, as well as Fab fragments, or the product of an Fab expression library.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art which provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY,* Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against caYAE1 may be employed to inhibit and/or treat infections, particularly fungal infections and especially candidosis (candidiasis), for example, superficial candidosis; candidosis of the oropharynx, such as, oral thrush (acute pseudomembraneous cancodosis), denture stomatitis, angular choilitis (perlèche), Candida leukoplakia (chronic hyperplastic candidosis), midline glossitis (median rbomboid glossitis, glossal central papillary atrophy, "antibiotic sore tongue", acute atrophic candidosis), and miscellaneous forms of oral candidosis; candidosis of the genitalia, such as, vulvovaginal candidosis (vaginal thrush, Candida colpitis), and candidosis of the penis (Candida balanitis, balanoposthitis and urethritis); candidosis of the skin, nails and other external sites, such as, Candida intertrigo, napkin (diaper) dermatitis, Candida onychia and paronychia, candidosis of the external ear, and miscellaneous cutaneous forms of candidosis; chronic mucocutaneous candidosis; systemic candidosis; candidosis of the gastrointestinal tract, such as, esophageal candidosis, gastric candidosis, candidosis of the intestine, Candida cholecystitis, and the "autobrewery syndrome" ("meiteisho"); candidosis of the Urinary Tract, such as, renal candidosis (Candida pyelonephritis), candidosis of the urinary bladder (Candida cystitis), Candida urethritis and prostatitis; cardiovascular Candida infections, such as, candida endocarditis, and myocarditis; Candida endocariditis, Candida myocarditis and pericarditis, Candida phlebitis and thrombophlebitis; Candida infections of the eye, such as, Candida endophthalmitis, Candida infections of the cornea and conjuctiva, and candidosis of the lacrimal sacs (dacryocystitis); candidosis of the central nervous system; Candida meningitis, cerebral candidosis, and candidosis of the inner ear; Candida infections of bones and joints; Candida peritonitis, hepatitis and miscellaneous other forms of systemic candidosis, such as, Candida peritonitis, Candida hepatitis and splenitis, Candida pancreatitis, Congenital and intrauterine candidosis (Candida chorioamnionitis and funisitis); disseminated candidosis, such as, in neonates, young infants, and heroin addict; Candida alergy, such as cutaneous Candida allergy and "candidids", Respiratory tract allergy to "Candida", Candida alergy in other bodily sites, "chronic candidosis" and "the yeast connection."

Polypeptide derivatives include antigenically, epitopically or immunologically equivalent derivatives which form a particular aspect of this invention. The term "antigenically equivalent derivative" as used herein encompasses a polypeptide or its equivalent which will be specifically recognised by certain antibodies which, when raised to the protein or polypeptide according to the present invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation , with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or derivative thereof is modified to make it less immunogenic in the individual. For example, if the individual is human the antibody may most preferably be "humanized"; where the complimentarity determining region(s) of the hybridoma-derived antibody has been transplanted into a human monoclonal antibody , for example as described in Jones, P. et al. (1986), Nature 321, 522–525 or Tempest et al.,(1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem 1989:264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

caYAE1-binding molecules and assays

This invention also provides a method for identification of molecules, such as binding molecules, that bind caYAE1. Genes encoding proteins that bind caYAE1, can be identified by numerous methods known to those of skill in the art, for example, ligand panning and FACS sorting. Such methods are described in many laboratory manuals such as, for instance, Coligan et al., *Current Protocols in Immunology* 1(2): Chapter 5 (1991). Also, a labeled ligand can be photoaffinity linked to a cell extract. Polypeptides of the invention also can be used to assess caYAE1 binding capacity of caYAE1-binding molecules, in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be structural or functional mimetics.

Antagonists and agonists—assays and molecules The invention also provides a method of screening compounds to identify those which enhance (agonist) or block (antagonist) the action of caYAE1 polypeptides or polynucleotides, such as its interaction with caYAE1-binding molecules.

For example, to screen for agonists or antagonists, a synthetic reaction mix, a cellular compartment, such as a membrane, cell envelope or cell wall, or a preparation of any thereof, may be prepared from a cell that expresses a molecule that binds caYAE1. The preparation is incubated with labeled caYAE1 in the absence or the presence of a candidate molecule which may be a caYAE1 agonist or antagonist. The ability of the candidate molecule to bind the binding molecule is reflected in decreased binding of the labeled ligand. Molecules which bind gratuitously, i.e., without inducing the effects of caYAE1 on binding the caYAE1 binding molecule, are most likely to be good antagonists. Molecules that bind well and elicit effects that are the same as or closely related to caYAE1 are agonists. caYAE1-like effects of potential agonists and antagonists may by measured, for instance, by determining activity of a reporter system following interaction of the candidate molecule with a cell or appropriate cell preparation, and comparing the effect with that of caYAE1 or molecules that elicit the same effects as caYAE1. Reporter systems that may be useful in this regard include but are not limited to colorimetric labeled substrate converted into product, a reporter gene that is responsive to changes in caYAE1 activity, and binding assays known in the art.

Another example of an assay for caYAE1 antagonists is a competitive assay that combines caYAE1 and a potential antagonist with membrane-bound caYAE1-binding molecules, recombinant caYAE1 binding molecules, natural substrates or ligands, or substrate or ligand mimetics, under appropriate conditions for a competitive inhibition assay. caYAE1 can be labeled, such as by radioactivity or a colorimetric compound, such that the number of caYAE1 molecules bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing caYAE1-induced activities, thereby preventing the action of caYAE1 by excluding caYAE1 from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules.

Other potential antagonists include antisense molecules (see Okano, *J. Neurochem.* 56: 560 (1991); *OLIGODEOXY-NUCLEOTIDES AS ANTISENSE INHIBITORS OF GENE EXPRESSION*, CRC Press, Boca Raton, Fla. (1988), for a description of these molecules).

Preferred potential antagonists include compounds related to and derivatives of caYAE1.

In a particular aspect the invention provides the use of the polypeptide, polynucleotide or inhibitor of the invention to interfere with the initial physical interaction between a pathogen and mammalian host responsible for sequelae of infection. In particular the molecules of the invention may be used: i) in the prevention of adhesion of fungi, in particular gram positive fungi, to mammalian extracellular matrix proteins on in-dwelling devices or to extracellular matrix proteins in wounds; ii) to block essential protein mediated mammalian cell invasion by, for example, initiating phosphorylation of mammalian tyrosine kinases (Rosenshine et al., *Infect. Immun.* 60:2211 (1992); iii) to block fungal adhesion between mammalian extracellular matrix proteins and fungal essential proteins which mediate tissue damage; iv) to block the normal progression of pathogenesis in infections initiated other than by the implantation of in-dwelling devices or by other surgical techniques.

Each of the DNA sequences provided herein may be used in the discovery and development of antifungal compounds. The encoded protein upon expression can be used as a target for the screening of antifungal drugs. Additionally, the DNA sequences encoding the amino terminal regions of the encoded protein or Shine-Delgarno or other translation facilitating sequences of the respective MRNA can be used to construct antisense sequences to control the expression of the coding sequence of interest.

The antagonists and agonists may be employed for instance to inhibit candidosis (candidiasis), for example, superficial candidosis; candidosis of the oropharynx, such as, oral thrush (acute pseudomembraneous candodisis), denture stomatitis, angular choilitis (perlèche), Candida leukoplakia (chronic hyperplastic candidosis), midline glossitis (median rbomboid glossitis, glossal central papillary atrophy, "antibiotic sore tongue", acute atrophic candidosis), and miscellaneous forms of oral candidosis; candidosis of the genitalia, such as, vulvovaginal candidosis (vaginal thrush, Candida colpitis), and candidosis of the penis (Candida balanitis, balanoposthitis and urethritis); candidosis of the skin, nails and other external sites, such as, Candida intertrigo, napkin (diaper) dermatitis, Candida onychia and paronychia, candidosis of the external ear, and miscellaneous cutaneous forms of candidosis; chronic mucocutaneous candidosis; systemic candidosis; candidosis of the gastrointestinal tract, such as, esophageal candidosis, gastric candidosis, candidosis of the intestine, Candida cholecystitis, and the "autobrewery syndrome" ("meiteisho"); candidosis of the Urinary Tract, such as, renal candidosis (Candida pyelonephritis), candidosis of the urinary bladder (Candida cystitis), Candida urethritis and prostatitis; cardiovascular Candida infections, such as, candida endocarditis, and myocarditis; Candida endocariditis, Candida myocarditis and pericarditis, Candida phlebitis and thrombophlebitis; Candida infections of the eye, such as, Candida endophthalmitis, Candida infections of the cornea and conjuctiva, and candidosis of the lacrimal sacs (dacryocystitis); candidosis of the central nervous system; Candida meningitis, cerebral candidosis, and candidosis of the inner ear; Candida infections of bones and joints; Candida peritonitis, hepatitis and miscellaneous other forms of systemic candidosis, such as, Candida peritonitis, Candida hepatitis and splenitis, Candida pancreatitis, Congenital and intrauterine candidosis (Candida chorioamnionitis and funisitis); disseminated candidosis, such as, in neonates, young infants, and heroin addicts; Candida allergy, such as, cutaneous Candida allergy and "candidids", Respiratory tract allergy to "Candida", Candida allergy in other bodily sites, "chronic candidosis" and "the yeast connection."

Vaccines

Another aspect of the invention relates to a method for inducing an immunological response in an individual, particularly a mammal which comprises inoculating the individual with caYAE1, or a fragment or variant thereof, adequate to produce antibody to protect said individual from infection, particularly fungal infection and most particularly Candida infections. Yet another aspect of the invention relates to a method of inducing immunological response in an individual which comprises, through gene therapy, delivering gene encoding caYAE1, or a fragment or a variant thereof, for expressing caYAE1, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a caYAE1 or protein coded therefrom, wherein the composition comprises a recombinant caYAE1 or protein coded therefrom comprising DNA which codes for and expresses an antigen of said caYAE1 or protein coded therefrom.

The caYAE1 or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of fungal cell surface proteins in DNA constructs used in such genetic immunization experiments in animal models of infection with Candida albicans will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of Candida albicans infection in mammals, particularly humans.

The polypeptide may be used as an antigen for vaccination of a host to produce specific antibodies which protect against invasion of fungi, for example by blocking adherence of fungi to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The present invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain caYAE1, it is to be understood that this covers fragments of the naturally occurring protein and similar proteins with additions, deletions or substitutions which do not substantially affect the immunogenic properties of the recombinant protein.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about I mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant fungi shortly before insertion of an in-dwelling device. Treatment may be continued after surgery during the in-body time of the device. In addition, the composition could also be used to broaden perioperative cover for any surgical technique to prevent Candida wound infections.

Many orthopaedic surgeons consider that humans with prosthetic joints should be considered for antifungal prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antifungals in this situation.

In addition to the therapy described above, the compositions of this invention may be used generally as a wound treatment agent to prevent adhesion of fungi to matrix proteins exposed in wound tissue and for prophylactic use in dental treatment as an alternative to, or in conjunction with, antifungal prophylaxis.

Alternatively, the composition of the invention may be used to bathe an indwelling device immediately before insertion. The active agent will preferably be present at a concentration of 1 $\mu$g/ml to 10 mg/ml for bathing of wounds or indwelling devices.

A vaccine composition is conveniently in injectable form. Conventional adjuvants may be employed to enhance the immune response.

A suitable unit dose for vaccination is 0.5–5 $\mu$g/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of fungi containing the essential protein.

In order to facilitate understanding of the following example certain frequently occurring methods and/or terms will be described.

EXAMPLES

The present invention is further described by the following examples. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL,* 2nd Ed.; Cold Spring Harbor Laboratory Press, Cold Spring Harbor, N.Y. (1989).

Example 1

Library Production

The polynucleotide having the DNA sequence given in SEQ ID NO:1 was obtained from a library of clones of chromosomal DNA of *Candida albicans* strain B792 in YEp13. In some cases the sequencing data from two or more clones containing overlapping *Candida albicans* DNAs was used to construct the contiguous DNA sequence in SEQ ID NO:1. Libraries may be prepared by routine methods, for example: Methods 1, 2 and 3 below.

Total cellular DNA is isolated from *Candida albicans* B792 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl2351), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Method 3

Total cellular DNA is partially hydrolyzed with Sau3A to generate fragments for cloning into library vectors, and such fragments are size-fractionated according to standard procedures. These fragments are then ligated into the BamHI site of the vector, such as YEp13. The ligated mixture is used to transform *E. coli* and then amplified by standard procedures.

Example 2 scYAE1 Characterization

The scYAE1 gene was disrupted in a diploid strain and replaced by a selectable marker, HIS3, using homologous recombination. The heterozygous diploid was sporulated and viability was shown to go 2:2. Those spores which did survive were all negative for the selectable marker indicating that the disruption of scYAE1 resulted in inviability. The diploid was then transformed with a plasmid carrying scYAE1 and the selectable marker URA3 or ADE2. Spores were then rescued which had been deleted for the genomic copy of scYAE1 and which carried the scYAE1 gene on a plasmid. The strains carrying scYAE1 on a plasmid marked with URA3 were unable to lose the plasmid as shown by an inability to grow on 5-FOA. Only strains which are URA3 minus are able to grow in the presence of 5-FOA. The strains carrying scYAE1 on an ADE2 marked plasmid were also not able to lose the plasmid as shown by non-sectoring white plasmids. If the plasmid were lost cells would show the ade2 minus phenotype of accumulation of a red pigment (Methods in Enzymology 194, 281–318, 1991).

*S. cerevisiae* YAE1 protein is tagged and this tagged version is used in immunofluorescence studies to determine the cellular localization of the protein. Conditional alleles of scYAE1 may be identified and once identified are used as a basis for cell based sceens for anti-fungal compounds.

Example 3 caYAE1 Characterization

The caYAE1 gene on a YEp13 plasmid which replicates in *S. cerevisiae* and which carries the selectable marker LEU2, was introduced into *S. Cerevisiae* strains in which the genomic scYAE1 was deleted and growth was dependent upon a plasmid carrying scYAE1. These transformants were then assayed for the ability to lose the plasmid carrying the scYAE1 gene either by growth on 5-FOA or by accumulation of a red pigment. If the strain is able to grow in the absence of the plasmid carrying scYAE1 this would show that the caYAE1 gene was able to complement the scYAE1 deletion. No complementation was observed by these assays but this is believed to be due to the inability of *S. cerevisiae* to utilize the *C. albicans* promoter. The caYAE1 gene was therefore expressed from the *S. cerevisiae* CUP1 promoter (Gene 48, 13–22,1986) and complementation assays were performed as described above. When expressed from a *S. cerevisiae* promoter, such as that of CUP1, the caYAE1 gene is able to complement deletion of the scYAE1 gene.

What is claimed is:

1. An isolated polynucleotide encoding a polypeptide comprising the amino acids of SEQ ID NO:2.

2. A vector comprising the nucleotide of claim 1.

3. A host cell comprising the vector of claim 2.

4. A process for producing a polypeptide comprising the step of expressing from the host cell of claim 3 a polypeptide encoded by said DNA.

5. A process for producing a cell which expresses a polypeptide comprising the step of transforming or transfecting the cell with the vector of claim 2 such that the cell expresses the polypeptide encoded by the nucleotides contained in the vector.

6. The isolated polynucleotide of SEQ ID NO:1.

7. An isolated polynucleotide comprising nucleotides 201 through 737 inclusive as set forth in SEQ ID NO:1.

8. An isolated polynucleotide consisting of nucleotides 201 through 737 inclusive as set forth in SEQ ID NO:1.

9. An isolated polynucleotide comprising nucleotides 1 through 797 inclusive as set forth in SEQ ID NO:1.

10. An isolated polynucleotide consisting of nucleotides 1 through 797 inclusive as set forth in SEQ ID NO:1.

11. A probe comprising an isolated polynucleotide selected from the group consisting of: at least 30 bases of the polynucleotide sequence set forth in SEQ ID NO: 1 and at least 50 bases of the polynucleotide sequence set forth in SEQ ID NO: 1.

12. A probe consisting of an isolated polynucleotide selected from the group consisting of: at least 30 bases of the polynucleotide sequence set forth in SEQ ID NO: 1 and at least 50 bases of the polynucleotide sequence set forth in SEQ ID NO: 1.

13. A vector comprising the polynucleotide of claims 7 or 9.

14. A host cell comprising the vector of claim 13.

15. A process for producing a response regulator polypeptide comprising the step of culturing a host cell of claim 14 under conditions sufficient for the production of said polypeptide.

16. A polynucleotide which is fully complementary to a polynucleotide of claims 1, 3, 4, 5, 6, 11 and 12.

\* \* \* \* \*